United States Patent [19]

Mason et al.

[11] Patent Number: 4,701,534

[45] Date of Patent: Oct. 20, 1987

[54] AZETIDINE DERIVATIVE

[75] Inventors: Ronald F. Mason, Ashford, England; Gary Scholes, The Hague; Jan W. van Reijendam, Amsterdam, both of Netherlands

[73] Assignee: Shell Oil Company, Houston, Tex.

[21] Appl. No.: 859,663

[22] Filed: May 5, 1986

Related U.S. Application Data

[63] Continuation-in-part of Ser. No. 743,735, Jun. 12, 1985, Pat. No. 4,665,197.

[30] Foreign Application Priority Data

Jun. 19, 1984 [GB] United Kingdom ............... 8415615
May 7, 1985 [GB] United Kingdom ............... 8511527

[51] Int. Cl.$^4$ ............................................ C07D 205/04
[52] U.S. Cl. .................................................. 548/950
[58] Field of Search ................... 260/239 A; 549/370, 549/371; 548/950, 958

[56] References Cited

U.S. PATENT DOCUMENTS 4,591,457  5/1986  Scholes et al. ...................... 548/950

FOREIGN PATENT DOCUMENTS 214933   5/1961  Austria ............................... 548/950
1140049  1/1969  United Kingdom .

Primary Examiner—Glennon H. Hollrah
Assistant Examiner—D. B. Springer

[57] ABSTRACT

2-Benzyl-7,7-dimethyl-6,8-dioxa-2-aza-spiro[3,5]nonane of the formula

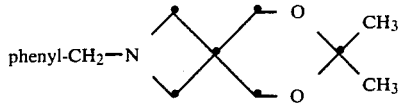

and a process for the preparation of that compound, which compound is useful as an intermediate in the preparation of 3-carboxy azetidine.

1 Claim, No Drawings

AZETIDINE DERIVATIVE

This application is a continuation-in-part of copending application Ser. No. 743,735, filed June 12, 1985, now U.S. Pat. No. 4,665,197.

BACKGROUND OF THE INVENTION

It is known from European patent application No. 29265 that 3-carboxyazetidine and related compounds are chemical hybridizing agents, their mode of action presumably being based on their ability to produce male sterility in plants. That application also describes a process for their preparation, starting from 3-cyano-1-diphenyl-methylazetidine, which may be prepared by methods known per se. Although the process described works well, it is not ideally suited for large scale preparations, since the bulky diphenylmethyl group on the nitrogen atom is removed only in the last of a series of steps, which means that in all but the last step large equipment is needed. Moreover, the parent starting compound diphenylmethylamine is relatively expensive.

It is the object of the invention therefore to provide an improved process for the preparation of a 3-carboxyazetidine compound, which is achieved firstly by the provision of novel intermediates and secondly by the provision of a process for their preparation, starting from readily available compounds.

DESCRIPTION OF THE INVENTION

The present invention relates to an N-benzyl dioxane spiro azetidine, namely the novel compound 2-benzyl-7,7-dimethyl-6,8-dioxa-2-aza-spiro[3,5]nonane, of the formula

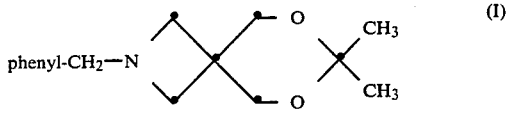
(I)

Compound I also can be named as 3,3-bis(hydroxymethyl)-1-benzyl-azetidine acetone acetal.

The invention also relates to a process for the preparation of this dioxane spiro azetidine, which comprises heating a dibromo dioxane derivative of the formula

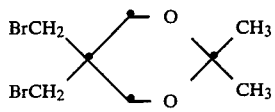

with benzylamine in an organic solvent and in the presence of an acid acceptor.

The function of the acid acceptor is to act as scavenger for the hydrogen bromide generated in the ring closure reaction. If benzylamine is used in sufficient excess, this reagent itself can provide the necessary hydrogen bromide scavenging, and can also function as the organic solvent. However, there are other solvents and acceptors which are often more economic and/or technically preferable. The organic solvent may be polar or non-polar, but in general the use of a polar solvent such as dimethyl sulphoxide or dimethyl formamide is found to lead to a much more rapid rate of reaction. Non-polar solvents, such as toluene and xylene, on the other hand, are often cheaper and under some conditions may improve the percentage conversion to the desired product.

The acid acceptor is suitably a base, conveniently an inorganic base, such as a hydroxide, carbonate or bicarbonate of sodium or potassium, although certain organic amines (such as benzylamine) can be used as base. The use of very strong organic bases having a pKa (measured in aqueous solution at 25° C.) above 16, such as potassium tert. butoxide, may lead to unwanted side reactions, and therefore significantly lower yields of the desired product.

The choice of solvent and acceptor may sometimes be interrelated, since it has been found that, in general, when a polar organic solvent is used, the yields and/or reaction times are better when the acceptor is a less strong base (such as sodium bicarbonate). Conversely, when a non-polar solvent, such as xylene, is used, better results may be obtained by using as acceptor a stronger base such as sodium hydroxide.

The temperature of the reaction is also an important aspect, since benzylamine will react with the bromo substituents only at a sufficiently elevated temperature. The choice of solvent system, and also the acceptor (base) used, can have an influence on the actual temperature at which a useful degree of reaction occurs; in general it is found that the temperature should be at least 80° C., and preferably over 100° C. In appropriate cases it may be convenient to carry out the reaction at the reflux temperature of the reaction medium.

The starting dibromo dioxane derivative of formula II may be prepared by appropriate adaptations of known synthetic procedures. A convenient synthesis route to this product is based on the reaction of pentaerythritol with hydrogen bromide, followed by reaction with acetone to form the dioxane, this procedure being described in application Ser. No. 743,735.

As mentioned above, compound I is a useful intermediate, which may be converted by known procedures to azetidine-3-carboxylic acid derivatives - compounds which exhibit plant growth regulant properties, especially the property of rendering sterile the male parts of plants. Suitable procedures for conversion of this dioxane spiro azetidine to the carboxylic acid include, for example, hydrolysis to the 3,3-bis(hydroxymethyl)-azetidine, oxidation, e.g. with nitric acid as described in copending application Ser. No. 743,735 or electrochemically as described in copending application Ser. No. 852,857, filed Apr. 16, 1986, followed by removal of the protective N-benzyl group, e.g. by catalytic hydrogenolysis.

The invention therefore includes also the use of compound I as an intermediate for the preparation of azetidine-3-carboxylic acid derivatives.

The invention is illustrated in the following Examples.

EXAMPLE 1

A mixture of 10 g of 2,2-bis(bromomethyl)-1,3-propanediol, 5 ml of acetone and a catalytic quantity (0.1 g) of p-toluenesulfonic acid was heated under reflux in 150 ml of benzene until the theoretical amount of water (0.8 ml) had been collected in a Dean-Stark trap (2 hours). Evaporation of the solvent gave 5,5-bis(bromomethyl)-2,2-dimethyl-1,3-dioxane (1A), as a solid, m.p.: 56°–58° C. The purity according to gas-liquid chromatography and proton NMR was 99%.

A mixture of 28.5 g of 1A, prepared by the procedures described above, and 12.0 g of sodium carbonate in 50 ml of dimethyl sulfoxide (DMSO) was heated to 135 2 C. To the mixture was added dropwise with stirring a solution of 13.5 g of benzylamine in 50 ml of DMSO over a period of 5 to 6 hours. When the addition had been completed the reaction mixture was stirred for 7 hours at 135° C. After cooling, 10 ml of water was added and the whole was extracted with pentane. The pentane extract was washed with water, dried and evaporated. Distillation of the residue under reduced pressure gave Compound I as a colorless oil b.p.: 135°–136° C. at 2 Torr.

EXAMPLE 2

75.5 g of 1A, prepared by the procedures described in Example 1, and 53.5 g of benzylamine were heated with stirring under nitrogen at 120°–125° C. for 5½ hours. The resulting mixture was diluted with 250 cc of toluene, cooled overnight, and the crystalline precipitate (benzylamine hydrobromide) filtered off and washed with toluene. The washings and the filtrated were combined and distilled in vacuo to separate unreacted starting material, yielding Compound I as an oil, b.p.: 115° C. at 0.1 Torr. This product was further characterized by its NMR spectrum (at 60 and 360 MHz); mass spectrum (M+ =247) and also elemental analysis:

Calculated for $C_{15}H_{21}NO_2$: C 72.9; H 8.5; N 5.7; Found C 70.6; H 8.6; N 5.5.

EXAMPLES 3–14

The procedure described in Example 1 was repeated, but substituting different solvents and/or bases, and with variations in the reaction time. The results of these experiments are summarized in Table 1.

| Example No. | Solvent | Base | Temp., °C. | Time, h. | Conversion of Dibromo Acetal % | Selectivity to Dioxane Spiro Azetidine % |
|---|---|---|---|---|---|---|
| 3 | DMF | NaHCO$_3$ | 120 | 2 | 60 | 35 |
| 4 | dioxane | NaOH | 101 | 20 | 20 | 90 |
| 5 | diglyme | NaHCO$_3$ | 135 | 6.5 | 35 | 30 |
| 6 | DMSO | KOH | 80 | 6 | >95 | 35 |
| 7 | DMSO | NaHCO$_3$ | 100 | 18 | 88 | 49 |
| 8 | DMSO | NaHCO$_3$ | 90 | 24 | 93 | 58 |
| 9 | DMSO | NaOH | 50 | 1.5 | 10 | 18 |
| 10 | DMSO | NaHCO$_3$ | 130 | 11 | 98 | 87 |
| 11 | DMSO | K$_2$CO$_3$ | 120 | 6 | 92 | 32 |
| 12 | DMSO | Na$_2$CO$_3$ | 125 | 6 | 90 | 32 |
| 13 | DMSO | NaHCO$_3$ | 130 | 12 | 98 | 83 |
| 14 | DMSO | NaHCO$_3$ | 135 | 4 | 88 | 85 |

(DMF = dimethyl formamide; DMSO - dimethyl sulfoxide)

EXAMPLE 15

A slurry of 276 g of 2,2-bis(bromomethyl)propane-1,3-diol, 184 g of acetone, 570 g of a paraffin solvent (a commercial mixture of C$_5$ to C$_8$ paraffinic hydrocarbons, boiling between 60° and 80° C.) and 1.1 g of para-toluenesulfonic acid was refluxed at atmospheric pressure. Water was separated from the distillate and the organic phase was returned. When no more water was formed, 2 g of anhydrous sodium carbonate was added to neutralize the acidic catalyst.

Solvent was removed by distilling to a pot temperature of 97° C. at atmospheric pressure. The remaining slurry was diluted with 210 g of xylene, to give a solution of 1A and some unconverted starting material in the ratio 98:2.

To the xylene solution of 1A were added 84 g of sodium hydroxide pellets and 106 g of anhydrous sodium carbonate. While stirring vigorously, this mixture was heated to reflux (140° C. pot temperature) and 113 g of benzylamine was added slowly over a period of 6 h.

Heating and stirring were continued for a further sixty six hours. From the distillate the aqueous phase was separated; the organic phase was returned to the reactor. The condenser temperature was 60° C.

At 24 h after beginning of the benzylamine addition 50 g of organic distillate was withdrawn from the reactor, to raise the pot temperature to 150°–155° C.

The resulting slurry of organic liquid and inorganic salts was cooled to 50° C. and 550 g of water were added. The aqueous phase was separated, extracted with 90 g of xylene and discarded. The combined organic layers were washed with 300 g of a 1% aqueous sodium hydroxide solution, and contained Compound 1 as the main component, together with some unconverted starting material.

The crude product solution was added slowly to a cold (0° C.) solution of 60 g sulfuric acid in 300 g of water. By cooling the temperature was kept at 5°–10° C.

After the addition, the organic phase was separated and stabilized by adding anhydrous sodium carbonate. Evaporation of the solvent yielded 34 g of a white crystalline solid, shown by NMR to consist of nearly pure 5,5-bis(bromomethyl)-2,2-dimethyl-1,3-dioxane (0.113 mol).

From the acidic aqueous phase the acetone, formed in the hydrolysis step, was distilled off under vacuum (20 Torr., 50° C. max.). Then a solution of 54 g (1.35 mol) of sodium hydroxide in 216 g of water was slowly added at 30° C. This caused formation of an organic layer (268 g) which was separated and mixed with 300 g of toluene. 68 g of water was removed from the product by Dean-Stark distillation.

At the same time, the liquid gradually became homogeneous and a precipitate of salts was formed, which was separated by filtration at 80° C.

The resulting filtrate was cooled to 20° C., which caused crytallization of the product. The crystals were washed with toluene and dried, to give 143 g (0.69 mol) of 1-benzyl-3,3-bis(hydroxymethyl)azetidine, m.p.: 85°–86° C. This product may be oxidized by either the nitric acid procedure of application Ser. No. 743,735 or the electrochemical procedure of application Ser. No. (K-577), and 3-carboxyazetidine obtained therefrom by removal of the protective benzyl group using conventional procedures.

What is claimed is:

1. 2-Benzyl-7,7-dimethyl-6,8-dioxa-2-aza-spiro[3,5-]nonane, of the formula

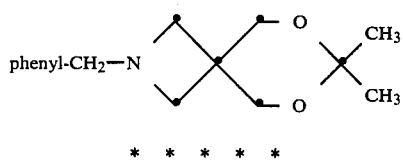

* * * * *